Figure 1:
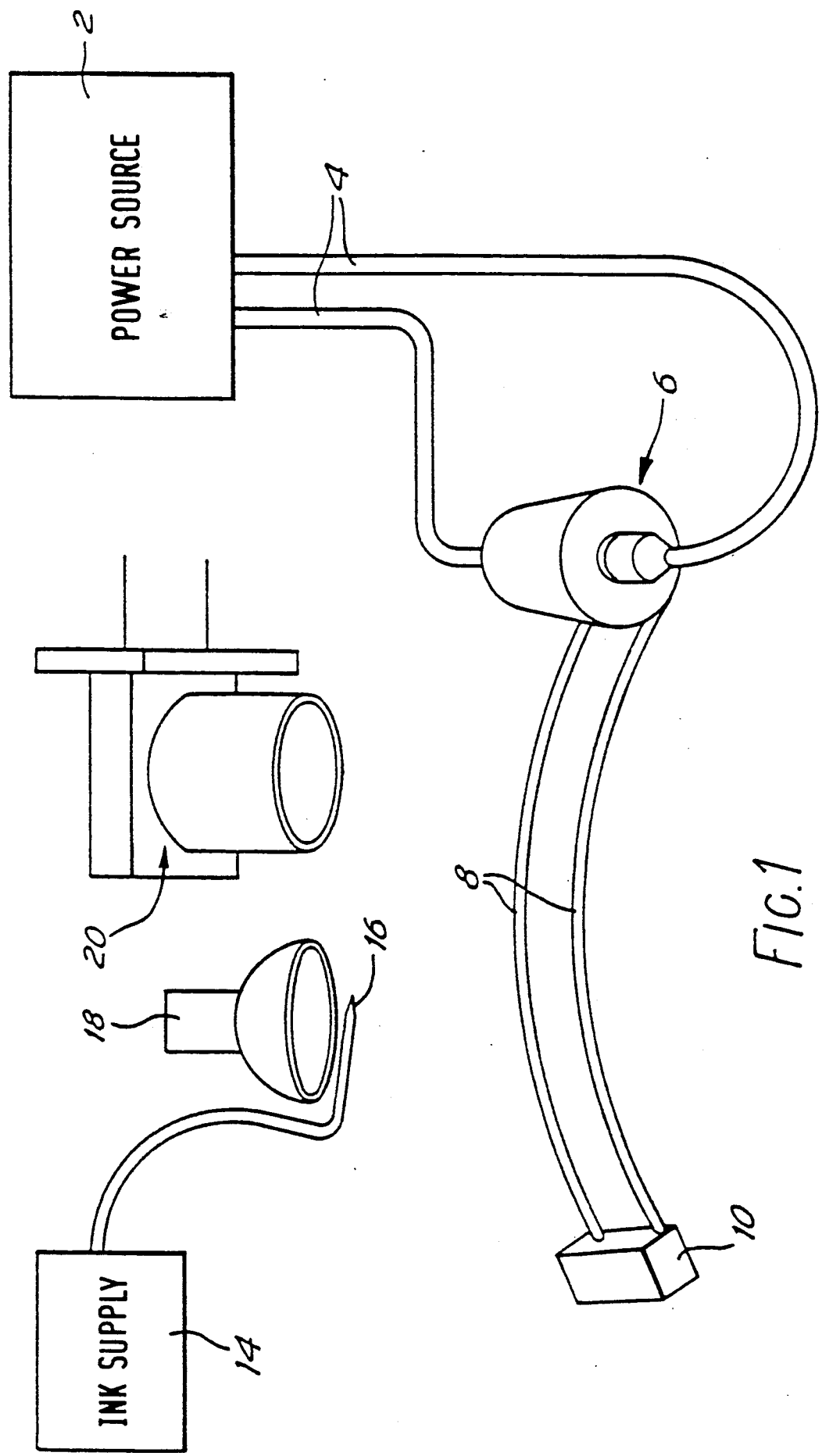

United States Patent [19]

Winchester

[11] Patent Number: 5,053,702
[45] Date of Patent: Oct. 1, 1991

[54] APPARATUS FOR MAGNETIC PARTICLE INSPECTION WITH AN ADJUSTABLE CABLE FOR MAGNETIZING INSPECTION AREAS OF VARIABLE DIMENSIONS

[75] Inventor: Richard G. J. Winchester, Newton Hill, United Kingdom

[73] Assignee: Amerada Hess Limited, London, United Kingdom

[21] Appl. No.: 382,633

[22] Filed: Aug. 7, 1989

[30] Foreign Application Priority Data

Oct. 26, 1987 [GB] United Kingdom ............... 8725040

[51] Int. Cl.$^5$ ..................... G01N 27/84; G01R 33/12
[52] U.S. Cl. ................................. 324/216; 324/228; 324/262
[58] Field of Search ............................ 324/214–216, 324/262, 228

[56] References Cited

U.S. PATENT DOCUMENTS 2,258,274 10/1941 Betz ........................................ 324/262
3,167,161 1/1965 Appleton ............................. 191/12.2
3,337,695 8/1967 Brown .................................. 191/12.4
4,388,593 6/1983 Mittleman ............................ 324/216

FOREIGN PATENT DOCUMENTS 2079945 1/1982 United Kingdom .
2182445 5/1987 United Kingdom .

OTHER PUBLICATIONS

Patent Abstracts of Japan, vol. 8, No. 33, p. 254, Abstract of JP 58-189554, 11/1983.

Primary Examiner—Walter E. Snow
Attorney, Agent, or Firm—Nixon & Vanderhye

[57] ABSTRACT

A magnetic particle inspection system includes apparatus for applying a magnetic field to an inspection area of a metal structure. This apparatus comprises a power cable arranged in at least one cable inspection loop to which electrical power is connected. In this way the adjacent inspection area is magnetized. The inspection aea is sprayed with disclosing fluid and an ultra violet light illuminates the sprayed area. The length of the cable inspection loop is adjustable so that the area of the inspection area can be varied. The apparatus is particularly designed to be mounted on a remotely operated vehicle.

28 Claims, 2 Drawing Sheets

APPARATUS FOR MAGNETIC PARTICLE INSPECTION WITH AN ADJUSTABLE CABLE FOR MAGNETIZING INSPECTION AREAS OF VARIABLE DIMENSIONS

The present invention relates to a magnetic particle inspection system, and to a cable unit for use in such a system.

Particularly in underwater environments, magnetic particle inspection systems are used for discerning cracks or stresses in metal structures, such as oil rigs.

The traditional means of performing magnetic particle inspection in underwater conditions is to use divers, and, as this often requires saturation diving techniques, is expensive and subjects the divers to physical risk.

The present invention seeks to provide a magnetic particle inspection system which can be used on a remotely operated vehicle.

According to a first aspect of the present invention there is provided a cable unit for use in a magnetic particle inspection system, said cable unit comprising a cable arranged to form at least one loop, and means for connecting the cable to receive electrical power, the cable unit further comprising means for enabling the length of said loop to be adjusted.

In an embodiment, the length of the or each loop can be adjusted to be in the range of substantially 0 to 1 meter.

In one embodiment, the cable forms a single loop which is defined by two limbs which extend substantially parallel to each other. However, if preferred, the cable may be arranged to form two or more adjacent loops, each being defined by two substantially parallel limbs, with the limbs of all of the loops extending substantially parallel to one another. The cable unit further comprises means to tension the loop or loops of cable.

In an embodiment, the cable unit has a housing in which said cable can be received The two ends of the cable are coupled to connector means for connecting electrical power thereto Spring means are provided to tension the cable, and preferably these spring means are received within the housing.

The looped end of the cable is preferably fixed to a cable grip which can be pulled away from the housing of the cable unit to pull the cable out of the housing against the action of the spring means.

It will be appreciated that the cable unit can be suitably mounted on a remotely operated vehicle. If then a moveable part, such as a manipulator, of that vehicle engages the cable grip, the cable can be pulled out of the housing to form a loop or loops of cable of the length required. Subsequent application of electrical power to the cable enables an area adjacent thereto to be subjected to a magnetic field so that it can be inspected by magnetic particle inspection techniques.

The present invention also extends to a magnetic particle inspection system incorporating a cable unit as defined above, and further comprising means for spraying ink or other disclosing fluid onto an area adjacent the looped cable, and illuminating means.

According to a further aspect of the present invention there is provided a magnetic particle inspection system comprising means for spraying a disclosing fluid, means for illuminating an area on which the fluid has been sprayed, and means for applying a magnetic field to the sprayed area, said magnetic field applying means comprising a power cable connectible to receive electrical power, the apparatus further comprising means for enabling the length of said power cable to be adjusted.

In an embodiment, said cable is arranged to form at least one loop whose length can be adjusted. Preferably, the length of the loop or loops of cable can be adjusted to be in the range of 0 to 1 meter.

In an embodiment, the cable in said magnetic particle inspection system is provided in a cable unit as defined above.

The illuminating means is preferably an ultra violet light.

A camera, which may be a video camera or a photographic camera is arranged to view the inspected area and make records of the results obtained.

Figure 2:
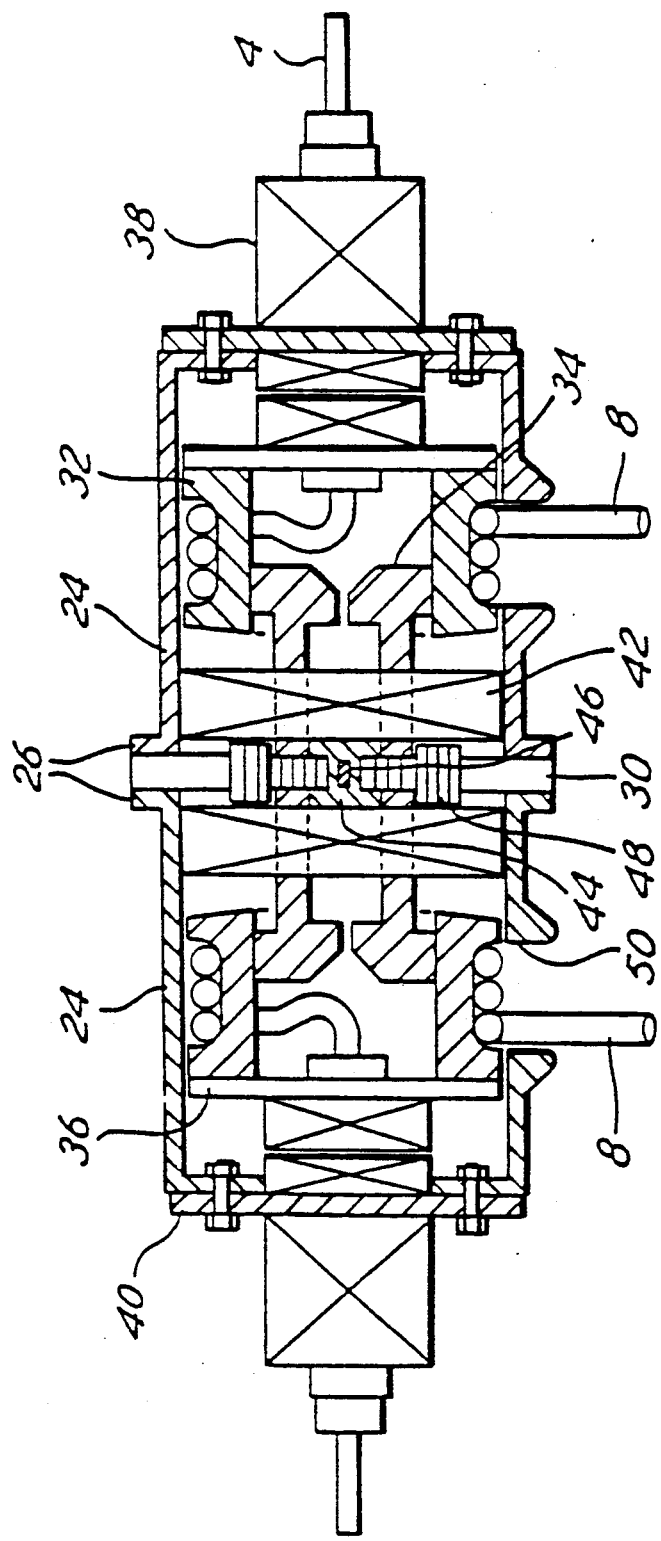

Embodiments of the present invention will hereinafter be described, by way of example, with reference to the accompanying drawings, in which: FIG. 1 shows schematically a magnetic particle inspection incorporating the present invention, and FIG. 2 shows a longitudinal section of the cable unit of the system of FIG. 1.

It is know to inspect metal structures for cracks or stresses by a magnetic particle inspection technique. A magnetic field is applied to the surface under test and an ink incorporating both magnetic particles and fluorescing particles is sprayed onto the surface which is then illuminated by ultra violet light. Stresses and cracks produce gaps in the magnetic field in which the ink settles, and when the surface is illuminated by ultra violet these ink particles fluoresce.

This magnetic particle inspection technique is well know and will not therefore be further described herein.

Generally, when this technique is used subsea, for example, to inspect oil rigs, divers take a length of wire and wind it around a structure to be inspected, the wire then being connected to an electrical supply. The diver then arranges for the spraying of ink, its illumination, and the inspection of the results, for example, by the use of video cameras.

The magnetic particle inspection system illustrated in FIG. 1 is designed for use on a remotely operated vehicle (not illustrated). The system comprises an electrical power source 2 which is preferably mounted on the vehicle. In the embodiment illustrated, the power supply 2 is a secondary of a transformer mounted on the vehicle, the primary of the transformer being connected by way of a tether to a power supply at the surface.

The terminals of the supply 2 ar connected by way of cables 4 and a cable unit 6 to supply electrical power to a loop of a cable 8. The cable unit 6 is illustrated in FIG. 2 and will be described further hereinbelow. This cable unit 6 is also mounted on the vehicle. The cable unit 6 may be fixed on the frame or hull of the vehicle, or preferably is mounted on a movable part, such as a manipulator, of the vehicle.

A cable grip 10 is fixed to the looped end of the cable and is used to pull the cable 8 out of the cable unit 6 against spring tension As is described below, the arrangement is such that pulling on the cable grip 10 enables cable 8 to be pulled out of the cable unit 6 to form a loop whose length can be in the range 0 to 1 meter. The loop is defined by two limbs which are arranged to remain substantially parallel to one another and to remain tensioned. In this respect, it will be apparent from FIG. 1 that the two limbs of cable 8 arranged to exit from the cable unit 6 are spaced at a spacing from each other, and that they are similarly spaced with respect to one another at their looped end by way of the cable grip 10.

The magnetic particle inspection system of FIG. 1 also comprises an ink supply 14 which is suitably mounted on the remotely operated vehicle. This ink supply 14 comprises generally a flexible bag ink container (not illustrated) connected to an ink spray nozzle, indicated at 16, by way of a delivery pump (not shown). The ink spray nozzle 16 has spring loaded ball valves to prevent sea water entering into the ink bag whilst the pump is not running A substantially conventional ultra violet lamp 18 is also mounted on the vehicle and is arranged to illuminate the area which has been sprayed with ink. In addition, a substantially conventional high resolution video camera, represented at 20, which may be either colour or black and white, is also mounted on the vehicle.

If the vehicle is provided with three or more manipulators it is preferred that the ink nozzle 16, the ultra violet lamp 18 and the video camera all be mounted on the central one of the three manipulators, with the cable unit 6 mounted on another of the manipulators, and the cable grip 10 engageable by the remaining manipulator.

In use, the manipulator carrying the cable unit 6 positions this unit at one end of an area to be inspected. The third manipulator then engages the cable grip 10 and pulls out the loop of cable 8 from the unit 6 against spring tension to the length required. The area to be inspected, adjacent to the loop, is then sprayed with ink by way of the nozzle 16 and the cable 8 energised by way of the supply 2. The area under inspection is illuminated by way of the lamp 18 and inspected by way of the video camera 20. Of course, a photographic camera could be provided in addition to or in place of the video camera 20.

A longitudinal section of the cable unit 6 is shown in FIG. 2. It will be seen that the cable unit comprises a housing formed by two cylindrical housing sections 24 made out of stainless steel. The two housing sections 24, which are substantially identical in size and shape, are arranged such that radially extending flanges 26 provided at one end of each section are arranged to face each other. The two flanges 26 are bolted together to secure therebetween a centre plate 30.

Within each housing section 24 is mounted a cable drum 32 made of stainless steel and around which up to 1 meter of cable 8 is wound. Each drum 32 is mounted on one end of a hollow shaft 34 and is rotationally fixed thereto. Each drum 32 is also attached to a rotatable end plate 36 of a respective slip ring assembly 38 for electrically connecting each cable 4 from the supply 2 to one end of the looped cable 8. A non-rotating plate 40 of each slip ring assembly 38, which are standard single pass, subsea units, is bolted to the outside of the respective housing section 24.

Each hollow shaft 34 is supported in a nylon split bearing 42 which is push fitted into the respective housing enclosure 24 and held in place by a circlip (not shown). The ends of the two hollow shafts 34 are connected by a two piece axle stub 44 to effectively form a continuous shaft supporting the two cable drums 32. The two pieces of the axle stub 44 are linked by way of a push fit, square section drive pin 46.

The axle stub 44 is the axle not only for the shafts 34 but also for a spring assembly 48. For this reason its central, reduced section portion, defined by the drive pin 46, is of square section. The spring assembly 48 is constructed as a spiral clock type unit which is retained within the centre plate 30. Thus, rotation of the shafts 34 and axle 44 in one direction will effectively "wind up" the spring. Rotation in this tension applying, one direction can be achieved by pulling out the cable 8 through guide openings 50 provided in the housing sections 24. Pulling out the cable in this manner is achieved by pulling the cable grip 10 away from the cable unit 6 as described above. When the pull on the cable grip 10 is released, the spring action will rewind the cable back onto the drums 32. The two cable drums 32, the spring assembly 48, and their associated shafts effectively form a spring tensioned winch for the cable.

It will be appreciated that the spring tension can be preset by winding the shafts 34 and axles 44 before the two halves of the cable unit are bolted together by way of the centre plate 30. Similarly, as the spring weakens through use it can be reset by the same method.

As described above, the unit 6 is preferably mounted by suitable means onto one of the manipulators of a remotely operated vehicle, for example, onto its tool table.

In the embodiment illustrated, the cable is arranged to form a single loop defined by two limbs which extend substantially parallel to each other. However, it will be appreciated that, if required, the cable may be arranged to form two or more adjacent loops each being defined by two substantially parallel limbs, with the limbs of all of the loops extending substantially parallel to one another. For example, if two adjacent loops of cable are required they can be housed in a cable unit formed by appropriately interconnecting two of the winches described above.

It will be appreciated that other variations and modifications can be made to the embodiment of the invention described above within the scope of the present invention.

I claim:

1. Magnetic particle inspection apparatus comprising a cable unit having a housing, and a length of power cable received within said housing, aid power cable being arranged to extend through openings in said housing to defined at least one cable inspection loop extending externally of said housing, said cable unit further comprising electrical connector means for coupling to an electrical power supply, said electrical connector means being supported by said housing and being electrically coupled to said power cable for applying electrical power to said power cable and to said externally extending cable inspection loop, and further comprising means for selectively adjusting the length of said cable inspection loop externally of said housing whereby the dimensions of an inspection area influenced by said inspection loop when electrical power is applied thereto are variable.

2. Magnetic particle inspection apparatus as claimed in claim 1, wherein the length of said cable inspection loop can be adjusted to be in the range of substantially 0 to 1 meter.

3. Magnetic particle inspection apparatus as claimed in claim 1 or 18 wherein said means for selectively adjusting the length of said cable inspection loop comprises means to tension said cable inspection loop.

4. Magnetic particle inspection apparatus as claimed in claim 1, wherein said power cable is arranged to define a single inspection loop externally of said housing, said cable inspection loop being defined by two cable limbs which extend substantially parallel to each other.

5. Magnetic particle inspection apparatus as claimed in claim 4, further comprising spring means received within said housing and arranged to tension said power cable, and wherein said electrical connector means are arranged to couple electrical power to the two ends of said power cable.

6. Magnetic particle inspection apparatus as claimed in claim 5, further comprising two cable drums mounted within said housing and arranged for rotation about a common axis, said power cable being wound around said two cable drums, and wherein said spring means comprises a spring assembly interposed between said two cable drums and arranged to oppose rotation of said cable drums about said common axis in a direction to unwind said power cable from the drums.

7. Magnetic particle inspection apparatus as claimed in claim 6, wherein said electrical connector means comprises a respective slip ring assembly carried by each said cable drum.

8. Magnetic particle inspection apparatus as claimed in claim 5, wherein said means for selectively adjusting the length of said cable inspection loop comprises a cable grip fixed to the looped end of said cable inspection loop for pulling the power cable out of the housing through the openings against the action of said spring means.

9. A magnetic particle inspection system incorporating magnetic particle inspection apparatus as claimed in claim 1, and further comprising means for spraying ink or other disclosing fluid onto an inspection area adjacent to and influenced by the cable inspection loop, and illuminating means.

10. A magnetic particle inspection system comprising means for spraying a disclosing fluid, means for illuminating an inspection area on which the fluid has been sprayed, and magnetic particle inspection apparatus for applying a magnetic field to the sprayed inspection area, said magnetic particle inspection apparatus comprising a power cable connectible to receive electrical power, said power cable being arranged to define at least one cable inspection loop to be arranged adjacent said inspection area, and further comprising means selectively adjusting the length of said cable inspection loop whereby the dimensions of said inspection area are variable.

11. A magnetic particle inspection system as claimed in claim 10, wherein the length of the or each loop of power cable can be adjusted to be in the range of 0 to 1 meter.

12. A magnetic particle inspection system as claimed in claim 10, wherein the illuminating means comprises an ultra violet light.

13. A magnetic particle inspection system as claimed in claim 4, further comprising a camera arranged to view the illuminated area and make records of the results obtained.

14. A magnetic particle inspection system comprising means for spraying a disclosing fluid, means for illuminating an inspection area on which the fluid has been sprayed, and magnetic particle inspection apparatus for applying a magnetic field to the sprayed inspection area, said magnetic particle inspection apparatus comprising a cable unit having a housing, and a length of power cable receive within said housing, said power cable being arranged to extend through openings in said housing to define at least one cable inspection loop extending externally of said housing, said cable unit further comprising electrical connector means for coupling to an electrical power supply, said electrical connector means being supported by said housing and being electrically coupled to said power cable for applying electrical power to said power cable and to said externally extending cable inspection loop, and further comprising means for selectively adjusting the length of said cable inspection loop externally of said housing whereby the dimensions of an inspection area influenced by said inspection loop when electrical power is applied thereto are variable.

15. A magnetic particle inspection system as claimed in claim 14, wherein the length of the or each said cable inspection loop can be adjusted to be in the range of 0 to 1 meter.

16. Magnetic particle inspection apparatus comprising a cable unit having a housing, and a length of power cable received within said housing, said power cable being arranged to extend through openings in said housing to define a single cable inspection loop extending externally of said housing, said cable unit further comprising electrical connector means for coupling to an electrical power supply, said electrical connector means being supported by said housing and being electrically coupled to said power cable for applying electrical power to said power cable and to said externally extending cable inspection loop, and further comprising means for selectively adjusting the length of said cable inspection loop externally of said housing in the range of substantially 0 to 1 meter whereby the dimensions of an inspection area influenced by said inspection loop when electrical power is applied thereto are variable.

17. Magnetic particle inspection apparatus as claimed in claim 16, further comprising spring means received within said housing and arranged to tension said power cable, and wherein said electrical connector means are arranged to couple electrical power to the two ends of said power cable.

18. Magnetic particle inspection apparatus as claimed in claim 17, further comprising two cable drums mounted within said housing and arranged for rotation about a common axis, said power cable being wound around said two cable drums, and wherein said spring means comprises a spring assembly interposed between said two cable drums and arranged to oppose rotation of said cable drums about said common axis in a direction to unwind said power cable from the drums.

19. Magnetic particle inspection apparatus as claimed in claim 18, wherein aid electrical connector means comprises a respective slip ring assembly carried by each said cable drum.

20. Magnetic particle inspection apparatus comprising a cable unit having a housing, and a length of power cable received within said housing, said power cable being arranged to extend through openings in said housing to define a single cable inspection loop extending externally of said housing, said cable unit further comprising electrical connector means for coupling to an electrical power supply, said electrical connector means being supported by said housing and being electrically coupled to said power cable for applying electrical power to said power cable and to said externally extending cable inspection loop, and further comprising means for selectively adjusting the length of said cable inspection loop externally of said housing whereby the dimensions of an inspection area influenced by said inspection loop when electrical power is applied thereto are variable, wherein said cable inspection loop is defined by two cable limbs which extend substantially parallel to each other, and said electrical connector means are arranged to couple electrical power to the two ends of said power cable, and further comprising two cable drums mounted within said housing and arranged for rotation about a common axis, said power cable being wound around said two cable drums, and spring means received within said housing and arranged to tension said power cable, said spring means comprising a spring assembly interposed between said two cable drums and arranged to oppose rotation of said cable drums about said common axis in a direction to unwind said power cable from the drums.

21. Magnetic particle inspection apparatus comprising a cable unit having a housing, and a length of power cable received within said housing, said power cable being arranged to extend through openings in said housing to define at leas tone cable inspection loop extending externally of said housing, said cable unit further comprising electrical connector means for coupling to an electrical power supply, said electrical connector means being supported by said housing and being electrically coupled to said power cable for applying electrical power to said power cable and to said externally extending cable inspection loop, and further comprising means for selectively adjusting the length of said cable inspection loop externally of said housing whereby the dimensions of an inspection area influenced by said inspection loop when electrical power is applied thereto are variable, and further comprising two cable drums mounted within said housing and arranged for rotation about a common axis, said power cable being wound around said two cable drums, and wherein a spring assembly is interposed between said two cable drums and arranged to oppose rotation of said cable drums about said common axis in a direction to unwind said power cable from the drums.

22. Magnetic particle inspection apparatus as claimed in claim 20 or 21, wherein said electrical connector means comprises a respective slip ring assembly carried by each said cable drum.

23. Magnetic particle inspection apparatus as claimed in claim 20 or 21, wherein said means for selectively adjusting the length of said cable inspection loop comprises a cable grip fixed to the looped end of said cable inspection loop for pulling the power cable out of the housing through the openings against the action of said spring means.

24. A magnetic particle inspection system comprising means for spraying a disclosing fluid, means for illuminating an inspection area on which the fluid has been sprayed, and magnetic particle inspection apparatus for applying a magnetic field to the sprayed inspection area, said magnetic particle inspection apparatus comprising a cable unit having a housing, and a length of power cable received within said housing, said power cable being arranged to extend through openings in said housing to define at least one cable inspection loop extending externally of said housing, said cable unit further comprising electrical connector means for coupling to an electrical power supply, said electrical connector means being supported by said housing and being electrically coupled to said power cable for applying electrical power to said power cable and to said externally extending cable inspection loop, and further comprising means for selectively adjusting the length of said cable inspection loop externally of said housing in the range of 0 to 1 meter whereby the dimensions of an inspection area influenced by said inspection loop when electrical power is applied thereto are variable.

25. A magnetic particle inspection system comprising means for spraying a disclosing fluid, means for illuminating an inspection area on which the fluid has been sprayed, and magnetic particle inspection apparatus for applying a magnetic field to the sprayed inspection area, said magnetic particle inspection apparatus comprising a cable unit having a housing, and a length of power cable received within said housing, said power cable being arranged to extend through openings in said housing to define at least one cable inspection loop extending externally of said housing, said cable unit further comprising electrical connector means for coupling to an electrical power supply, said electrical connector means being supported by said housing and being electrically coupled to said power cable for applying electrical power to said power cable and to said externally extending cable inspection loop, and further comprising means for selectively adjusting the length of said cable inspection loop externally of said housing whereby the dimensions of an inspection area influenced by said inspection loop when electrical power is applied thereto are variable, and wherein said cable unit comprises two cable drums mounted within said housing and arranged for rotation about a common axis, said power cable being wound around said two cable drums, and a spring assembly interposed between said two cable drums and arranged to oppose rotation of said cable drums about said common axis in a direction to unwind said power cable from the drums.

26. A magnetic particle inspection system as claimed in claim 14 or 24, wherein the illuminating means comprises an ultra violet light.

27. A magnetic particle inspection system as claimed in claim 14 or 24, further comprising a camera arranged to view the inspection area and make records of the results obtained.

28. A magnetic particle inspection system as claimed in claim 15 or 24, wherein said cable unit comprises two cable drums mounted within said housing and arranged for rotation about a common axis, said power cable being wound around said two cable drums, and a spring assembly interposed between said two cable drums and arranged to oppose rotation of said cable drums about said common axis in a direction to unwind said power cable from the drums.

* * * * *